US005788959A

United States Patent [19]

Singh

[11] Patent Number: 5,788,959
[45] Date of Patent: Aug. 4, 1998

[54] DRUG DELIVERY DEVICE AND METHOD FOR EMPLOYING THE SAME

[75] Inventor: Manish Singh, Columbia, Md.

[73] Assignee: University of Maryland, Baltimore County, Baltimore, Md.

[21] Appl. No.: 426,980

[22] Filed: Apr. 24, 1995

[51] Int. Cl.[6] .......................... A61K 9/08; A61K 38/17; A61K 38/19; A61K 38/22

[52] U.S. Cl. .......................... 424/85.1; 424/85.2; 424/85.4; 424/425; 424/484; 424/486; 424/487; 424/488; 424/178.1; 514/3; 514/8; 514/12; 514/21; 514/773; 514/774; 514/777; 514/779

[58] Field of Search .......................... 424/400, 422, 424/423, 424, 425, 426, 484, 488, 499, 78.08, 85.1, 85.2, 85.4, 85.5, 85.7, 130.1, 485, 486, 487, 178.1; 514/777, 772.3, 8, 12, 21, 3, 773, 779, 774, 772.1, 782.788; 530/351, 384, 387.1

[56] References Cited

U.S. PATENT DOCUMENTS

| Re. 35,338 | 9/1996 | Haynes | 424/450 |
|---|---|---|---|
| 3,608,063 | 9/1971 | Banker | 424/22 |
| 4,164,559 | 8/1979 | Miyata et al. | 424/428 |
| 4,291,013 | 9/1981 | Wahling et al. | 424/426 |
| 4,347,234 | 8/1982 | Wahling et al. | 424/426 |
| 5,015,476 | 5/1991 | Cochrum et al. | 424/423 |
| 5,041,292 | 8/1991 | Feijen | 424/484 |
| 5,080,888 | 1/1992 | Grollier et al. | 424/61 |
| 5,358,706 | 10/1994 | Marlin et al. | 424/78.04 |
| 5,614,204 | 3/1997 | Cochrum | 424/423 |
| 5,645,827 | 7/1997 | Marlin et al. | 424/78.04 |
| 5,709,854 | 1/1998 | Griffith-Cima et al. | 424/93.7 |

OTHER PUBLICATIONS

Rosenblatt et al. "Chain Rigidity and Diffusional Release in Biopolymers Gels" *Proceed. Intern. Symp. Control. Rel. Bioact. Mater.*, 20:264–265 (1993).

Rosenblatt, "Mesh Size Measurement in Rigid and Flexible Polyelectrolyte Matrices" *ACS Conference*, Denver, Poster (1993).

Singh et al. "Polypeptide Delivery from Collagen: Electrostatic Effects", *Proceed. Intern. Symp. Control. Rel. Bioact. Mater.*, 20 (July 1993), pp. 107–108.

Singh et al. "Diffusion and Desorption Controlled Peptide Release from Collagen Matrices", *Proceed. Intern. Symp. Control. Rel. Bioact. Mater.*, 21 (1994), pp. 300–301.

Singh et al. "A Fundamental Study of Electrostatic Effects in the Release of Charged Polypeptides from Collagen Hydrogels", ACS Meeting (May 1994).

Singh et al. "Release of Polypeptides Via an Instantaneous Desorption Coupled with Diffusion Mechanism from Collagen Hydrogels", AICHE Meeting (Nov. 1994).

O'Shea et al. Ecapsulation of Rat Isfets of Langerhans Prolongs Xenograft Survival in Diabetic Mice. Diabetes. Aug. 1986, vol. 35, pp. 943–946.

*Primary Examiner*—Jeffrey E. Russel
*Attorney, Agent, or Firm*—Sughrue, Mion, Zinn, Macpeak & Seas, PLLC

[57] ABSTRACT

The present invention relates a drug delivery device which comprises a single phase matrix of two oppositely charged polymers (one positive and one negative), which releases a drug by combined mechanisms employing hindered diffusion, swelling and erosion. The present invention also relates to a method for employing these devices.

29 Claims, 5 Drawing Sheets

DRUG DELIVERY DEVICE AND METHOD FOR EMPLOYING THE SAME

FIELD OF THE INVENTION

The present invention relates to a drug delivery device for the sustained release of pharmaceutically active ingredients. In particular, the present invention relates to a drug delivery device comprising a single phase matrix of two oppositely charged polymers (one positive and one negative). The delivery device releases drugs by the combined mechanisms of hindered diffusion, swelling and erosion. This invention also relates to a method for employing these devices.

BACKGROUND OF THE INVENTION

Release of drugs enclosed in polymeric matrices is important in many biochemical and biomedical applications. The term "drug" as used herein refers to any substance which has pharmaceutical activity such as, for example, a protein. A "protein" as used herein is defined as a macromolecule comprising sequences of amino acids connected by peptide linkages. The term "polymer" used herein refers to a protein (e.g., polypeptide) or biopolymer. Additionally, the term "biopolymer" as used herein describes polymers that are produced by biological systems or are derived from biological starting materials. Examples of biopolymers include, for example, nucleic acids, polysaccharides and polyphosphates.

Following implantation of the drug delivery device, and due to the difference in the concentration gradient of the amount of drug in the matrix relative to the amount of drug in the surrounding tissues, there is a driving force for the drug to leave the polymeric matrix by diffusion.

This release of drug by diffusion is very rapid, and most of the drug is released from the matrix in a few hours. There are various ways to control the release of drug from a matrix, and this invention describes a novel way to modulate the release kinetics.

When the distance between the neighboring polymer units (mesh size) is larger than the size of the drug, the release rate is fast due to free diffusion. If the mesh size is smaller than the size of the diffusing species, the rate of release of the drug is decreased, because there is an increase in diffusional hinderance. When a charged polymer is present in solution, there is repulsion due to similar charges, and the polymer is present in an expanded state. These solutions have large mesh sizes which cause little or no hinderance to the diffusing drug. In addition, these polymeric solutions (when not cross-linked) diffuse out in physiological environments relatively fast, thus releasing drugs at high rates. For example, U.S. application Ser. No. 08/265,848, filed Jun. 24, 1994, now abandoned discloses another drug delivery device comprising a single phase matrix of a negatively-charged rigid polymer and a negatively-charged flexible polymer. (See also Singh et al, Proceedings of Controlled Release Society, Washington, D.C., pp. 107–108, (1993)).

In the present invention, addition of a second polymer which has a net opposite charge to the first polymer solution increases the stability of the matrix, as well as decreases the mesh size. The oppositely charged polymers of the present invention bind to each other due to electrostatic interaction, and act as electrostatic cross-linking agents which contract the entire system. This decrease in mesh size can be used to retard the release kinetics, and the increased stability can be used to deliver the drug over prolonged time. Further, these devices swell with time due to osmotic pressure, and this influx of solvent opens the meshwork leading to diffusion of entrapped drug.

After a certain time, when matrix has imbibed sufficient solvent, the three dimensional structure of the matrix of the present invention collapses, and leads to a burst in the release of drug. Thus, the devices for the present invention can release drug in a biphasic pattern where the hindered diffusion dominates initially, followed by opening of cage structures and a burst later.

Thus, the present invention can involve essentially three stages of release of the drug from the matrix. In the first stage, there is a retardation of release of drug due to the small mesh size, and the drug is released by hindered diffusion. In the second stage, the mesh size increases due to imbibement of solvent, and release of the drug occurs by free diffusion or less hindered diffusion. In the third stage, the matrix erodes, and the drug entrapped inside the matrix bursts out into the body.

The devices of the present invention can deliver drugs over extended periods of time, and by manipulating the two polymer concentrations, it is possible to modulate the release kinetics to obtain desired release rates.

All U.S. patents, publications, and pending U.S. patent applications referred to herein are hereby incorporated by reference.

SUMMARY OF THE PRESENT INVENTION

Accordingly, an object of the present invention is to provide a drug delivery device which allows for sustained release of a pharmaceutically active ingredient by the mechanisms of hindered diffusion coupled with swelling and erosion.

Another object of the present invention is to provide a method for sustained release of a pharmaceutically active ingredient in vivo over a prolonged period of time.

An additional object of the present invention is to provide a drug delivery device which can release a drug in a biphasic pattern, where hindered diffusion dominates initially, followed by opening of cage structures and a later burst.

These and other objects of the present invention, which will be apparent from the Detailed Description of the Invention provided below, have been met in one embodiment by a drug delivery device comprising a single phase matrix of a negatively-charged polymer and a positively-charged polymer.

DETAILED DESCRIPTION OF THE INVENTION

As discussed above, the objects of the present invention have been met, in one embodiment, by a drug delivery device comprising a single phase matrix of a positively-charged polymer and a negatively-charged polymer.

The device uses the electrostatic interactions between oppositely charged residues of the two polymers. However, this invention is not limited to only electrostatic interactions, and can also be extended to utilize hydrophobic interactions within regions of the charged polymers. Thus, the hydrophobic regions of one polymer can interact with the hydrophobic regions of the second polymer to exclude water from these regions. Polymers which have more than 5 hydrophobic residues, such as lysozyme, are referred to as hydrophobic region-containing polymers or proteins. Hydrophobicity is determined by the number of hydrophobic groups present on a molecule and is not related to charge. Lysozyme, for example, is a positively charged protein which also contains hydrophobic regions.

Figure 3:
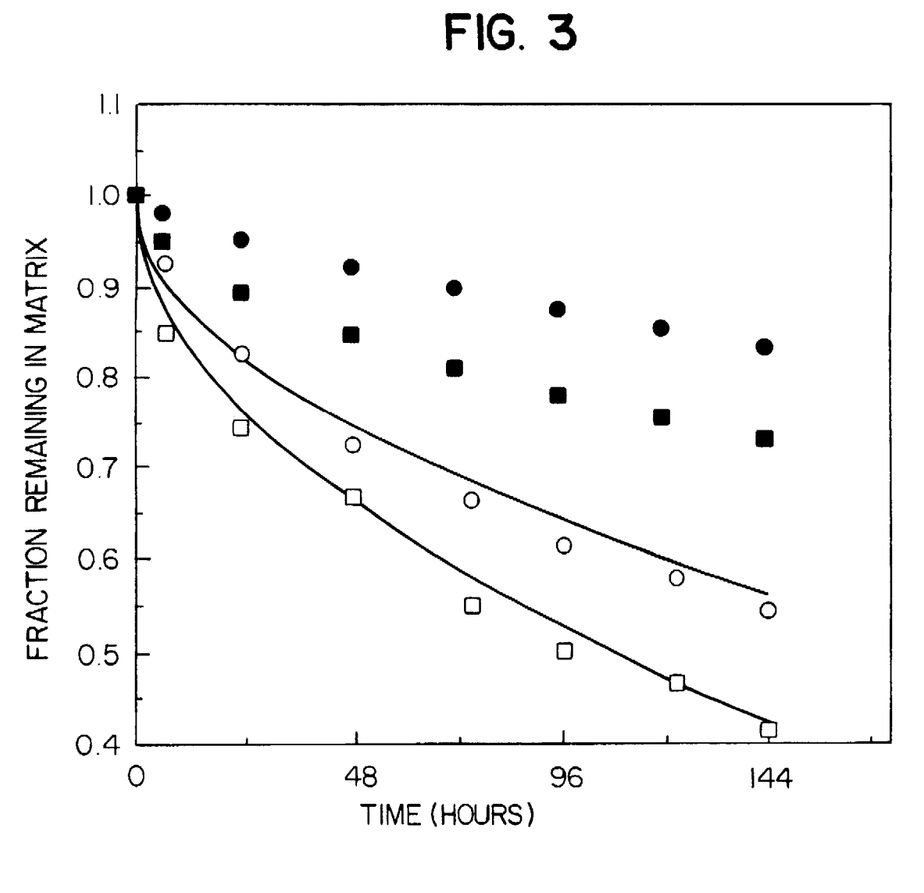
FIG. 3 shows the release of lysozyme (lysozyme; MW 14.5 kDa) from succinylated collagen matrices and native collagen matrices containing different concentrations of lysozyme. The data points represent the average of measurements performed in triplicate. The symbol □ represents native collagen having a loading equal to 0.06 mg/ml. The symbol ○ represents succinylated collagen having a loading equal to 0.06 mg/ml. The symbol ■ represents native collagen having a loading equal to 0.5 mg/ml, and the symbol ● represents succinylated collagen having a loading of 0.5 mg/ml.

As will be discussed in detail below, FIG. 3 shows a similar device which uses the hydrophobic interactions between native collagen, having a net neutral charge, and lysozyme. The hydrophobic interactions also lead to a reduction in the mesh size, which can be utilized to obtain sustained release of a drug. This device uses a novel mechanism to deliver a drug over a long time period in vivo. The release mechanism is a combination of hindered diffusion, swelling and erosion. In addition, charged drug desorption can also be utilized as one of the mechanisms in combination with others. It should also be noted that two or more drugs can be delivered simultaneously.

The phrase "negatively-charged", as used in the present invention, means that the polymer has a negative charge at about pH 6 to 8 or more than 5 negatively-charged residues. For a polymer to be used as a "negatively charged" polymer, it must have a higher number of negative charges compared to the number of positive charges.

The phrase "positively-charged", as used in the present invention, means that the polymer has a net positive charge at about pH 6 to 8 or has more than 5 positively-charged residues. For a polymer to be used as a "positively-charged" polymer, it must have a higher number of positive charges compared to the number of negative charges.

The charges on the two oppositely-charged polymers must be sufficient to bring about an electrostatic interaction.

An example of a negatively-charged polymer employed in this invention is succinylated collagen. Collagen is a naturally-occurring structural protein with a molecular weight of approximately 300 kDa. The net charge on collagen is near neutral with large numbers of positively and negatively-charged residues uniformly distributed along the entire length of the collagen molecule.

Collagen can be negatively-charged by succinylating it according to the procedure described in U.S. Pat. No. 4,164,559. This is a simple method to introduce negatively-charged groups on collagen. However, reagents other than succinic anhydride can be employed to make collagen negatively-charged as well.

For example, sulfosuccinimidyl acetate or sulfosuccinimidyl-3-(4-hydroxyphenyl)propionate (Bolton-Hunter reagent) can also be utilized according to the procedure described in Thompson et al, Biochem., 26:743–750 (1987). These compounds make collagen negatively-charged by blocking positive groups from ionizing. Alternatively, glutaric anhydride can be used in place of succinic anhydride by following the same procedure as used in succinylating collagen. The specific process to treat collagen is not critical to the present invention; all that is necessary is a process which can provide a negatively-charged collagen at about pH 6 to 8.

Examples of other negatively-charged polymers which can be used in the present invention include negatively-charged chitosan derivatives, such as carboxymethylated chitosan. The derivatives can be made by changing positive charges to negative charges by adding functional negative groups such as carboxylic acid, succinic acid or sulfonic acid to the polymer to make it negatively charged. For example, chitosan is carboxymethylated in order to obtain a net negative charge. Any polymer which has a negative charge at about pH 6 to 8 can be used.

Other examples of negatively-charged polymers which can be used in the present invention include hyaluronic acid, polyacrylic acid, sodium alginate, chondroitin sulfate, heparin and albumin.

Hyaluronic acid, sodium alginate, chondroitin sulfate and heparin all have an inherent negative charge. These negative charges are due to the presence of more than 5 carboxylic groups on the polymers.

Examples of positively-charged polymers used in the present invention include polylysine and lysozyme. Both have more than 5 amine groups which ionize to yield a net positive charge at about pH 6 to 8. Additional examples of positively-charged polymers include chitosan, a positively-charged collagen derivative such as methylated collagen, and positively-charged polyamino acids. Examples of suitable polyamino acids include homopolymers, such as polylysine and polyarginine, and heteropolymers such as random copolymers of arginine and lysine.

Well-known procedures can be used to methylate collagen thereby making it positively-charged. Chitosan is prepared by deacetylation of chitin which is a naturally occurring polysaccharide. Chitosan is also commercially available in biomedical grade which is biocompatible. Polylysine is preferably used as the positively-charged polymer in the drug delivery device of the present invention in view of biocompatibility and large charge density in the matrix.

Such biocompatibility indicates that there will be a minimal immune response by the host cells. Furthermore, a large charge density provides strong electrostatic interactions which lead to more stabilization of the matrix and smaller mesh sizes.

The polymers of the present invention can be cross-linked by any method. For example, the most commonly used agent to cross-link biopolymers and proteins is glutaraldehyde. Glutaraldehyde is reacted with the substrate at a slightly alkaline pH, and the cross-linking takes place in 5–30 minutes. (See Beauchamp et al. *Critical Reviews in Toxicology*, 22:143–174 (1992)). Other agents which can be used to cross-link biopolymers and proteins include, for example, dioxyl, isocyanates and imidoesters.

The drug delivery device of the present invention can be either surgically implanted or injected by using a syringe and a needle. Injectable devices are, of course, more convenient to utilize. If the concentrations of the two polymers are too high, they may not be injectable. However, generally the weight ratio should be about 0.05 to 1.0, and preferably about 0.1 to 0.5.

The upper molecular weight of the polymers is not critical to the present invention. The molecular weight of the polymers exemplified herein is approximately 10,000 to 5,000,000 daltons, and the preferred range is approximately 100,000 to 3,000,000 daltons.

The drug delivery device of the present invention can be prepared by combining a negatively-charged polymer and a positively-charged polymer in a single phase mixture, i.e., a homogeneous solution. The single phase mixture is prepared by mixing a solution of a negatively-charged polymer with a solution of a positively-charged polymer, by exchange between two vessels, e.g., two syringes. The drug is incorporated in the matrix by initially mixing it with one of the polymer solutions. Alternatively, the drug can also be incorporated after mixing the two polymers to make a homogeneous solution. This homogeneous solution is mixed with the drug by a simple exchange of two vessels, e.g., two syringes.

The device of the present invention is particularly effective for sustained release of very large growth factors, and also Factor VIII, Factor IX, and Protein C, since they would be hindered substantially by the mesh sizes of the polymeric combinations. The desired mode of administration of these factors is by subcutaneous implant. The device can also be used to deliver interferons, antibodies (e.g., IgG), interleukins, insulin, other growth factors, and erythropoietin. Examples of such other growth factors are human growth hormones, colony stimulating factor, and bone morphogenic protein. The net charge on the drug is not important as long as the drug is larger than the mesh size (i.e., 2–3 nm) of the matrix.

The molecular weight of the drug is generally greater than about 5,000 daltons. However, one skilled in the art would realize that the drug or specific pharmaceutically active ingredient utilized is not critical to the present invention. Thus, additional examples of pharmaceutically active ingredients which can be utilized include any drug larger than about 5,000 daltons, preferably about 5,000 daltons to 300,000 daltons. More preferably, the drug is between about 10,000 daltons to 100,000 daltons.

The particular amount of pharmaceutically active ingredient which can be loaded in the device of the present invention depends, inter alia, on the molecular weights and solubilities of the two polymers, as well as that of the pharmaceutically active ingredient. However, generally the amount of pharmaceutically active ingredient which can be loaded in the device of the present invention is about 0.0001% (w/v) to about 5.0% (w/v). Preferably, the amount of drug loaded is about 0.1% (w/v) to 1.0% (w/v). The minimum amount of drug loaded in the matrix depends on the specific drug, and its efficacy relating to dosage amount.

An example of a suitable positively-charged polymer, negatively-charge polymer and a positively-charge drug combination, for use in the present invention, is methylated collagen (positively-charged polymer), hyaluronic acid (negatively-charge polymer), and bone morphogenic protein (positively-charged drug).

An example of a suitable negatively-charged polymer, positively-charged polymer and negatively-charged drug combination, for use in the present invention, is carboxymethylated chitosan (negatively-charged polymer), polylysine (positively-charged polymer), and Factor IX (negatively-charged drug).

The combination of a negatively-charged polymer and a positively-charged polymer in a single phase matrix, in the present invention, provides the following benefits in controlling the release of a pharmaceutically active ingredient over a single phase polymer matrix containing only positive charges or only negative charges:

(i) It gives a smaller overall mesh size due to its ability to form electrostatic cross-links;

(ii) It more effectively inhibits diffusion of the drug due to the smaller mesh size;

(iii) The release rate is a coupled hindered diffusion with swelling and surface erosion. By manipulating the ratios of the two polymers, it is possible to obtain different swelling and erosion rates, as well as diffusion rates, which can be used to modulate the release kinetics;

(iv) For a charged drug, desorption can also be used as one of the release mechanisms;

(v) In contrast to a single polymer (non-cross-linked) implant which diffuses/dissolves very fast, the device of the present invention is more stable and lasts much longer; and (vi) In contrast to a cross-linked single polymer implant which has a very high viscosity, the mixed matrix is easily injected into a subject since it has a comparatively lower viscosity.

With respect to a full explanation of benefit (iv) above, it should be noted that if a negatively-charged drug is put into the matrix, it binds to the positively-charged polymer present. Furthermore, if a positively-charged drug is put into the matrix, it binds to the negatively-charged polymer present. The amount of drug present as the free drug, and the bound drug is in equilibrium with each other, and only the free drug would be available for diffusion into the surrounding fluid. This decreases the concentration gradient for diffusion, thereby lowering the rate of release. After some of the drug is diffused out, the amount of free drug decreases, and some of the bound drug desorbs to maintain the equilibrium. This desorbed drug becomes available for diffusion. Thus, the release mechanism of the present invention is a coupled diffusion and desorption which is more effective than diffusion alone.

Due to interactions of the two polymers, the combined polymer matrix is unexpectedly more effective at sustaining the release duration of pharmaceutically active ingredients of a size of 5,000 daltons or more, than devices composed of either polymer alone. The unexpectedly superior results provided by the presently claimed matrices are illustrated in the Examples and attached Figures.

In addition, the mixed matrix of the present invention can be easily injected via a syringe and needle into a subject intraperitoneally, or subcutaneously, intramuscularly and is naturally resorbed by the subject.

The preferred biopolymer matrices of the present invention, which are naturally resorbed in the body, eliminate the need for explant surgery once the drug has been delivered.

The following examples are provided for illustrative purposes only, and are in no way intended to limit the scope of the present invention.

EXAMPLE 1

Preparation of the Polymers

A. Negatively-charged Polymers

Collagen was negatively-charged by succinylating collagen following the procedure described in U.S. Pat. No. 4,164,559. Five grams of collagen were solubilized in 2.0 liters of acidified water (pH 3.0 HCl), and the pH was adjusted to 9.0 by the addition of NaOH. An acetone solution (100 ml) containing 1.0 g of succinic anhydride was then gradually added to the collagen suspension. During the addition of succinic anhydride, the pH of the collagen suspension was maintained at about 9.0 by the addition of NaOH.

The resulting succinylated collagen was concentrated by precipitation at a pH of 4.5, and centrifuged at 15,000× g at 20° C. The solvent containing acetone and water was replaced by phosphate buffer saline comprising 20 mM sodium phosphate and 130 mM sodium chloride (pH 7.0) (hereinafter "PBS") by exhaustive dialysis. The concentration of the succinylated collagen was measured by biuret assay.

B. Positively-charged Polymers

Poly-L-Lysine (MW 15,000–30,000 daltons) was purchased commercially (Sigma Chemical Company), and prepared by dissolving the desired amount in PBS.

Lysozyme was also purchased from Sigma and prepared by dissolving in an appropriate amount of PBS.

EXAMPLE 2

Single Phase Matrix Preparations for Examples 3–5

In order to prevent bacterial contamination, preparation of single phase matrices was performed under clean conditions in a laminar flow hood.

Single phase matrices were prepared by syringe-to-syringe exchange of premeasured volumes of the polymer solutions.

In Example 3, a succinylated collagen (21 mg/ml) and polylysine (2.0 mg/ml) single phase matrix was used to compare Differential Scanning Colorimetry thermograms with a succinylated collagen (21 mg/ml) matrix and a polylysine (2.0 mg/ml) matrix.

For preparation of the matrices of Example 4A, succinylated collagen stock solution was adjusted to a concentration of 22 mg/ml. Polylysine-FITC solutions were made using PBS in order to obtain concentrations of 2.0 mg/ml, 6.0 mg/ml, and 56 mg/ml. Then, the following three compositions were made for Example 4A using the following procedures:

(i) 3.5 g of succinylated collagen gel (22mg/ml was syringe mixed with 0.06 ml of polylysine-FITC solution (2.0 mg/ml) to obtain the following matrix composition:
succinylated collagen (21 mg/ml)+polylysine-FITC (0.035 mg/ml);

(ii) 3.5 g of succinylated collagen gel (22 mg/ml) was syringe mixed with 0.06 ml of polylysine-FITC solution (6.0 mg/ml) to obtain the following matrix composition:
succinylated collagen (21 mg/ml)+polylysine-FITC (0.1 mg/ml); and (iii) 3.5 g of succinylated collagen gel (22 mg/ml) was syringe mixed with 0.10 ml of polylysine-FITC solution (56 mg/ml) to obtain the following matrix composition:
succinylated collagen (21 mg/ml)+polylysine-FITC (1.55 mg/ml).

In order to prepare the matrices of Example 4B, succinylated collagen stock solution was adjusted to a concentration of 22 mg/ml. A native collagen stock solution was created having a concentration of 22 mg/ml, and lysozyme solutions in PBS were created having concentrations of 2.2 mg/ml and 18 mg/ml. Then, the following four compositions were made using the following procedures:

(i) 3.5 g of succinylated collagen gel (22 mg/ml) was syringe mixed with 0.1 ml of lysozyme (2.2 mg/ml) to obtain the following matrix:
succinylated collagen (21 mg/ml)+lysozyme (0.06 mg/ml);

(ii) 3.5 g of native collagen (22 mg/ml) was syringe mixed with 0.1 ml of lysozyme (2.2 mg/ml) to obtain the following matrix:
native collagen (21 mg/ml)+lysozyme (0.06 mg/ml);

(iii) 3.5 g of succinylated collagen gel (22 mg/ml) was syringe mixed with 0.1 ml of lysozyme (18 mg/ml) to obtain the following matrix:
succinylated collagen (21 mg/ml)+lysozyme (0.5 mg/ml); and (iv) 3.5 g of native collagen (22 mg/ml) was syringe mixed with 0.01 ml of lysozyme (18 mg/ml) to obtain the following matrix:
native collagen (21 mg/ml)+lysozyme (0.5 mg/ml).

In Example 5, Dextran-Fluorescein Isothiocyanate (Dextran-FITC) was used as the diffusing drug. Succinylated collagen (23 mg/ml) alone, and a succinylated collagen (21 mg/ml) and polylysine (2.0 mg/ml) single phase matrix were used to measure release kinetics of Dextran-FITC.

After mixing and homogenization, the resulting devices were allowed to equilibrate at 4° C for 2 days.

EXAMPLE 3

Differential Scanning Calorimetry (DSC)

In this Example, experiments were carried out to measure the thermal stability of the mixed matrices compared with single polymer solutions of succinylated collagen and polylysine. DSC is a direct method for studying the structure and thermal stability of the proteins and polymers. The melting of the intra-molecular structure is a specific property of proteins. The melting curves obtained in a DSC experiment can be used to quickly screen changes in protein tertiary structure (Privalov, *Pure Appl. Chem.*, 52:479–497 (1980)). If the melting temperature of the matrix is close to the physiological temperature, the matrix would not last for a long time at the site of implantation.

Melting endotherms of the succinylated collagen, polylysine and succinylated collagen-polylysine matrices prepared in Example 2 above were measured with a micro DSC (Hart Scientific, Pleasant Grove, Utah). The devices were placed in sample vials (0.3–1.0 ml) and the samples were scanned from 15° C. to 75° C. with a heating rate of 1° C./min. Since the complex formation between succinylated collagen and the positively-charged polypeptide, polylysine, forms a three dimensional network, it was postulated that such would be more stable compared to the succinylated collagen alone. The results are shown in FIGS. 1A–1C.

Figure 1A:
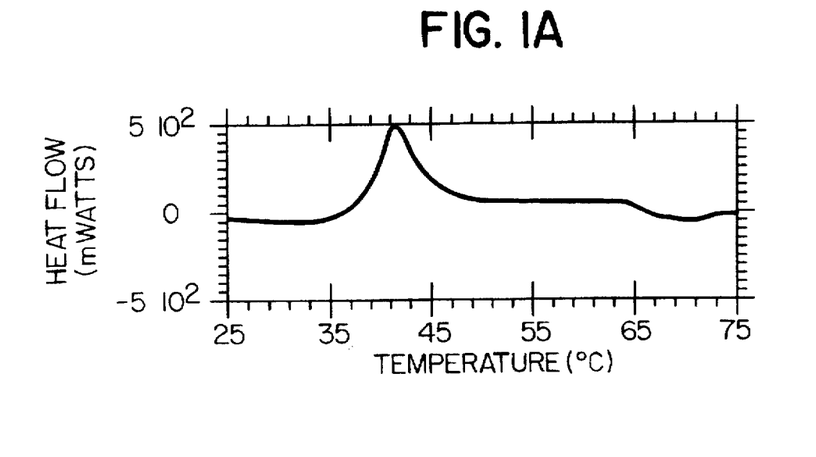
FIGS. 1A–1C show the DSC (Differential Scanning Calorimetry) thermograms for a succinylated collagen matrix (FIG. 1A), a polylysine matrix (FIG. 1B) and a succinylated collagen-polylysine single phase matrix (FIG. 1C).
Figure 1B:
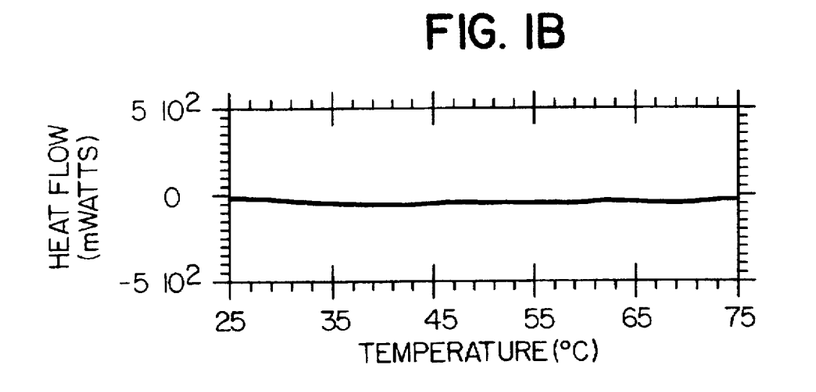
Figure 1C:
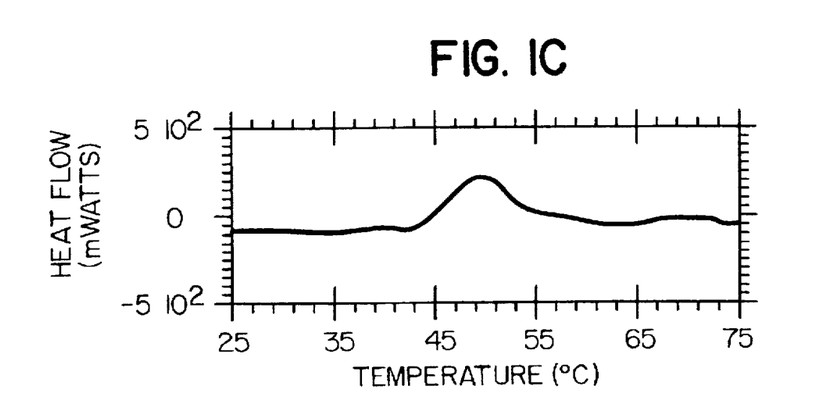

FIGS. 1A–1C show the curves obtained for thermal denaturation of a succinylated collagen matrix (FIG. 1A), a polylysine matrix (FIG. 1B) and a succinylated collagen-polylysine single phase matrix (FIG. 1C). The curves indicate an increase in conformational stability of the succinylated collagen-polylysine device compared to succinylated collagen alone. The conformation stability is characterized by the thermal denaturation temperature ($T_m$), which is the temperature corresponding to the peak maximum. The succinylated collagen endotherm (FIG. 1A) shows $T_m$ values around 41° C.–43° C. The polylysine endotherm (FIG. 1B) shows no peaks, indicating a lack of helices at physiological conditions and a random coil configuration. The succinylated collagen-polylysine single phase matrix (FIG. 1C) showed a melting temperature around 48°–50° C. This increase in $T_m$ value clearly demonstrates that the oppositely charged polylysine and succinylated collagen single phase matrix forms a three dimensional network which is more stable than either polymer solution alone. Thus, the increased stability indicates that the succinylated collagen-polylysine matrix can be used to deliver drugs over longer periods of time than the succinylated collagen matrix, as the latter matrix is degraded faster than the former.

EXAMPLE 4

(A) Release of Polylysine-FITC From Succinylated Collagen Matrices

The purpose of this example was to demonstrate that after a critical amount of polylysine (positively-charged polymer) has been added to the succinylated collagen matrix (negatively-charged polymer), the mesh size decreases sufficiently to hinder the motion of diffusing specie. This diffusional hindrance can be used to control the rate of release of drug from the matrix implant. This decrease in mesh size can be demonstrated by measuring polylysine-FITC release rates from drug delivery devices.

Succinylated collagen matrices with different concentrations of polylysine-FITC were prepared as described in Example 2, and the rate of release of polylysine-FITC was measured as described below.

1.0 ml of succinylated collagen-polylysine-FITC single phase matrix was placed in a 4.0 ml cylindrical vial. The interface was flattened and trapped air bubbles removed by mild centrifugation. Each matrix was equilibrated for 2 days prior to measuring release profiles. In vitro release experiments were performed by placing 1.0 ml of phosphate buffered saline (PBS) on top of 1.0 ml of matrix (ambient temperature). The buffer was removed every 6–24 hours, and replaced with fresh PBS. All release experiments were performed in triplicate. Mass balances were verified by assaying for the concentration of the remaining matrix, after release, by extracting the remaining polylysine-FITC probe. Extraction was performed by dissolving the remaining matrix in 5–10 ml of PBS. Polylysine-FITC concentration was analyzed using a fluorescence intensity reader at wavelengths of 485 nm and 535 nm. The results are shown in FIG. 2.

Figure 2:
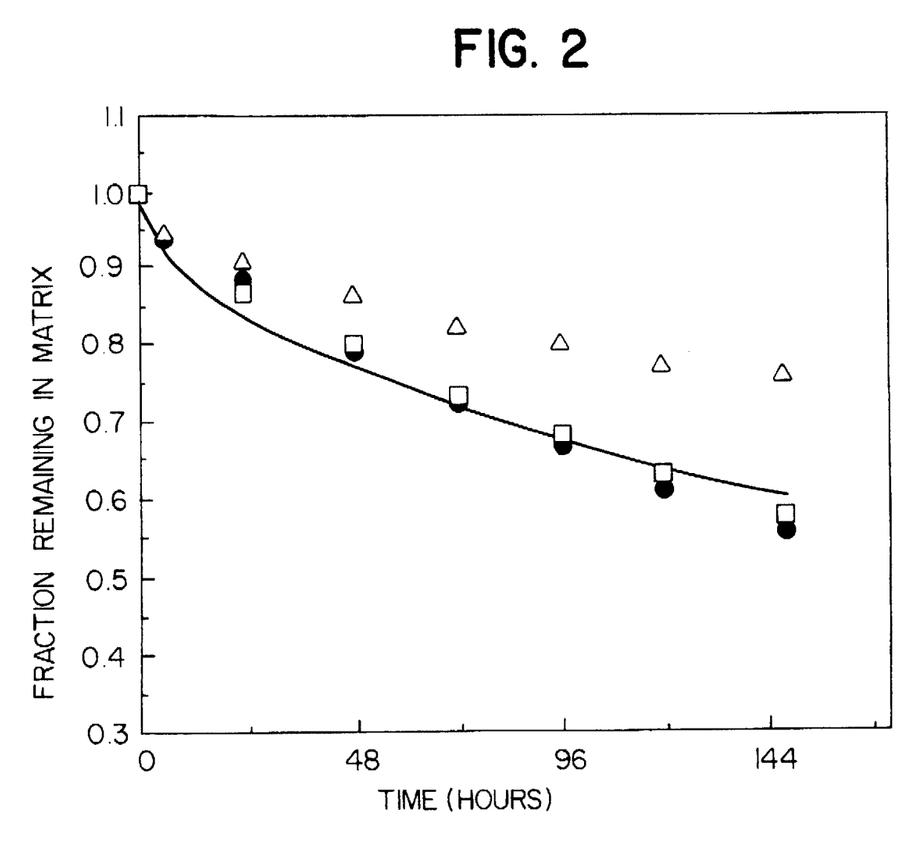
FIG. 2 shows the release of fluorescein-labeled polylysine (polylysine-FITC; MW 15–30 kDa) from succinylated collagen matrices containing various concentrations of polylysine-FITC. The data points represent the average of measurements performed in triplicate. The symbol ● represents an initial loading equal to 0.035 mg/ml. The symbol ◙ represents an initial loading equal to 0.10 mg/ml, and the symbol Δ represents an initial loading equal to 1.55 mg/ml.

FIG. 2 compares the release rates of polylysine-FITC from succinylated collagen matrices at different loading levels. The fraction remaining in the matrix was plotted against release time. The release experiments were conducted in PBS. The solid line indicates the model predictions for low concentrations of polylysine-FITC added ($\leq 2.0$ mg/ml) based on free solution diffusivity and adsorption isotherm measurements.

At low loading concentrations (0.035 mg/ml to 0.10 mg/ml), the release rates agree well with the model predictions. However, at a higher concentration (1.55 mg/ml), the release rates are much slower than model predictions. The matrices containing 1.55 mg/ml of polylysine-FITC were swollen at the end of the six day release experiment. After the matrices were contacted with the buffer, they swelled approximately 8–10% during the six days of release. In the case of low loadings of polylysine-FITC, i.e., 0.035 mg/ml to 0.10 mg/ml, the release rate was governed by a coupled free diffusion-desorption mechanism. However, in the case of higher loading (1.55 mg/ml), the release rates were slower due to increased hindered diffusion from succinylated collagen-polylysine-FITC meshwork. This clearly demonstrates that mixing a negatively-charged polymer with a positively-charged polymer decreases the mesh size, which can be used to sustain the release of drug molecules.

(B) Release Rate Measurements from Lysozyme-Collagen and Lysozyme-Succinylated Collagen Matrices The purpose of this experiment was to demonstrate that hydrophobic interactions between succinylated collagen and lysozyme (i.e., two oppositely charged polymers) can be used to modulate the mesh size of the matrix. Also, this experiment demonstrates that a combination of electrostatic interactions and hydrophobic interactions between succinylated collagen and lysozyme can be used to modulate the mesh size of the matrix which controls diffusion of drug species. This decrease in mesh size is demonstrated by measuring the lysozyme release rate from the composite matrices with different concentrations of lysozyme. A decrease in the fractional release rate by increasing the lysozyme concentration indicates that the mesh size has greatly reduced due to interactions between lysozyme and the other matrix polymer.

The experimental techniques were the same as those described in Example 4A except with respect to the polymer utilized.

The lysozyme and collagen matrices were prepared as described in Example 2.

The lysozyme concentration was analyzed by an activity assay on *Micrococcus lysodeikticus* suspension. Lysozyme dissolves the cell wall of *Micrococcus lysodeikticus*, thus increasing the turbidity. The optical density of the bacterial suspension was measured at 450 nm. The assay is very sensitive and can detect a concentration as low as 1.0 µg/ml of lysozyme.

FIG. 3 shows the release behavior of lysozyme from SC (succinylated collagen) and NC (native collagen) matrices for the different loadings of lysozyme (0.060 mg/ml and 0.50 mg/ml). The solid lines indicate the release behavior based on model predictions for free solution diffusivity and for adsorption isotherm parameters for the SC and NC matrices. For both the succinylated and native collagen matrices, higher loadings (0.5 mg/ml) showed slower release profiles compared to lower loadings (0.06 mg/ml). This result is similar to the polylysine result described above.

In particular, FIG. 3 illustrates the concept of using a combination of electrostatic and hydrophobic interactions to reduce the mesh sizes and to achieve an overall slower release profile of the drug. Lysozyme is used as the second polymer which has electrostatic interactions with succinylated collagen. By increasing the amount of lysozyme from 0.06 mg/ml to 0.5 mg/ml, the overall mesh size is decreased. This decrease in overall mesh size is illustrated by slower release of lysozyme when loaded at 0.5 mg/ml.

FIG. 3 also demonstrates the utility of hydrophobic interactions in decreasing the overall mesh size. When native collagen (neutral) is mixed with lysozyme (hydrophobic and positively charged), and the lysozyme concentration is changed from 0.06 to 0.5 mg/ml, there is a decrease in mesh size and a slower release profile.

Returning to release behaviors, it should be noted that those of polylysine and lysozyme at higher loadings (0.5 mg/ml) do not agree with theoretical model predictions (based on free diffusion coupled with desorption), and an additional mechanism governing release rate behavior controls the release kinetics. The lysozyme diffusivity is a function of the concentration of the lysozyme in solution. However, for small concentrations as low as 0.5–1.55 mg/ml, the difference in diffusivity from free solution values is too small to explain the much slower release rates that are encountered here (Hervert et al, *Phy. Rev. Lett.*, 42:1681 (1979)).

Polylysine and lysozyme both are positively-charged polypeptides which adsorb to negatively-charged succinylated collagen due to electrostatic interactions. These electrostatic interactions form an ionically stabilized three-dimensional network which has smaller pore sizes than a SC matrix alone. This network configuration then hinders the diffusion of the loaded polypeptide so that it no longer diffuses freely. Lysozyme is capable of forming a three-dimensional network with native collagen stabilized by hydrophobic interactions.

Also, it appears that the lysozyme adsorbed to collagen changes the content of both bound water and free water (or freezing water) in the matrix. In hydrogels, the free water is the only space available for drug diffusion, and its amount directly defines the space available for transport through the matrix (Pitt, *Int. J. Phar.*, 59:173–196 (1990)). The observation of swelling of the matrix at the end of drug release indicates that, on mixing positively-charged polypeptides with succinylated collagen, the free water content of the composite matrix decreases; and the matrix swells to reach equilibrium with the contacting buffer. This is in accord with recent findings of Mirejsky et al, *Current Eye Res.*, 10:187 (1991), who investigated the adsorption of lysozyme on contact lens materials, and found that the presence of lysozyme caused a decrease in the equilibrium water content. Their DSC thermograms indicate that the water content and the content of freezing water (free water) decreased. They also suggested a three-dimensional complex formation between lysozymes and contact lens polymers based on their DSC and permeability studies.

This phenomenon of altering the transport properties of a hydrogel by interaction with the loaded polypeptide, i.e., polylysine and lysozyme, has significance in the development of new biomaterials for drug delivery. Initially, due to complex formation, the collagen matrix is rigid and allows slow diffusion of the drug. However, as time progresses and the polypeptide is released into the outside environment, the diffusion becomes less hindered. This causes the diffusion coefficient to be a function of time or amount of polypeptide remaining in the matrix. Finally, after a critical concentration of the polypeptide is released, the hydrated collagen matrix collapses leading to another burst. This collapse of the matrix is similar to an incremental disintegration with time in the experimental geometry employed here. The polypeptide concentration will initially decrease below its critical value in about the top ⅓, and then in about the middle ⅓, followed by about the bottom ⅓ portion of the matrix. The spatial disintegration also proceeds in the same order with time. Thus, the release pattern is biphasic, and the second phase starts after a prolonged period of time, after a critical concentration has been released.

Since the disintegration proceeds spatially as a front, the second phase consists of a number of release phases stretched in time. This indicates a potential of developing drug delivery systems where the release rates can be modulated by manipulating both the concentrations of both polymers. Furthermore, in contrast to diffusional systems where the release rates decrease continuously with time, it is possible to maintain release rates closer to a zero order by carefully engineering a system where the release of one polymer modulates the drug diffusivity (i.e., the drug is admixed in a two polymer system). The modulated diffusion coupled with erosion can maintain a zero order release profile.

EXAMPLE 5

Investigations on Release Rate of Dextran

The purpose of this experiment is to show that a matrix composed of two oppositely charged polymers can be more effective in sustaining the release of the drug from such a matrix.

The release matrices were prepared as mentioned in Example 2. The procedures used for the release experiments were the same as those described in Example 4A with the exception of the polymer utilized.

Dextran-FITC was monitored using a fluorescence intensity reader at wavelengths of 485 nm and 535 nm.

Figure 4:
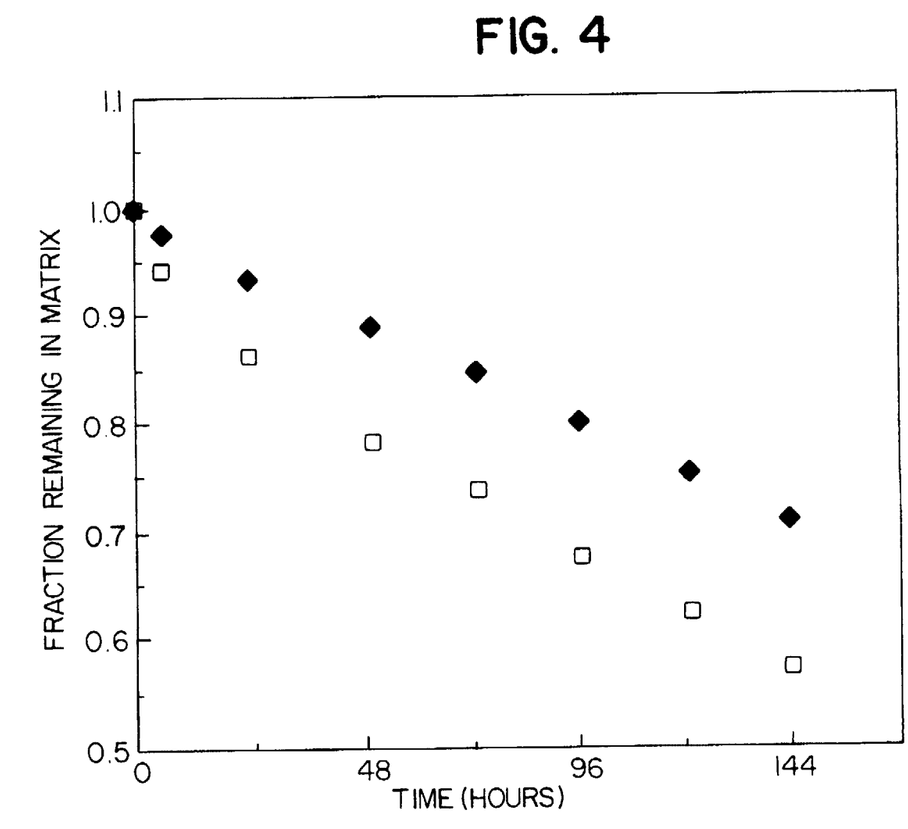
FIG. 4 shows the release rates of fluorescein-labelled dextran (FITC-DEXTRAN; MW 70 kDa) from a succinylated collagen matrix and a succinylated collagen-polylysine single phase matrix. The data points represent averages based on measurements performed in triplicate. The symbol ▣ represents a single phase matrix of succinylated collagen (23 mg/ml), and the symbol ♦ represents succinylated collagen (21 mg/ml) and polylysine (2.0 mg/ml).

Measurements of the release rate of dextran-FITC (MW 70 kDa) from succinylated collagen and succinylated collagen-polylysine matrix is shown in FIG. 4. This example demonstrates that succinylated collagen-polylysine matrix can provide sustained release of dextran-FITC.

Figure 5:
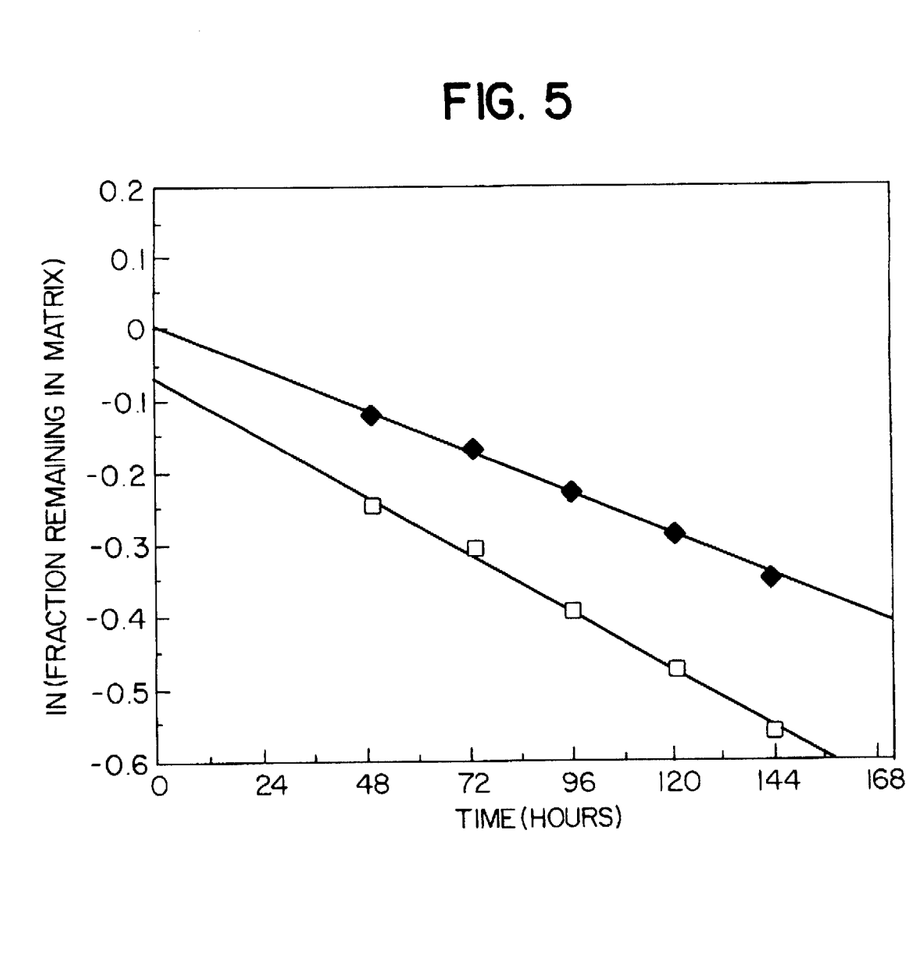
FIG. 5 shows the semi-log plot of ln (fraction of succinylated-collagen and polylysine, and succinylated collagen remaining in the matrices) versus time. The symbol ♦ represents a single phase matrix of succinylated collagen (21 mg/ml) and polylysine (2.0 mg/ml), and the symbol ▣ represents succinylated collagen (23 mg/ml).

FIG. 4 shows plots of fraction remaining in the matrix versus the time for six days. It shows a slower release profile for dextran-FITC from the composite matrix compared to the succinylated collagen alone matrix. Since dextran-FITC is not charged, it is not expected to interact with polylysine, which implies that the slower release is due to the hindered motion of dextran in the composite matrix. This was verified by replotting the release data on a semilog scale. A linear correlation on the semilog plot (as equation: ln (fraction remaining) $\sim -D\pi^2 t/4L^2$) indicates that the behavior is purely diffusional (Rosenblatt et al, *J. Controlled Release*, 9:195–203 (1989); and Crank, *The Mathematics of Diffusion*, Clarendon Press, Oxford (1975)). FIG. 5 shows the semilog plot for long periods of time (>36 hours), and shows linear behavior for succinylated collagen, as well as succinylated collagen-polylysine matrices. This linear behavior indicates that the release is primarily diffusion controlled. The hindered diffusion coefficients can be calculated using the above equation from the slopes on the semilog plots. The calculated values are $3.8 \times 10^{-7}$ cm$^2$/sec for succinylated collagen matrix and $2.6 \times 10^{-7}$ cm$^2$/sec for the succinylated collagen-polylysine matrices. These values are smaller than the free solution diffusivity of dextran ($4.5 \times 10^{-7}$ cm$^2$/sec) (Davidson et al, *Macromolecules*, 21:3474–3481 (1988)).

The complex formation between collagen and polylysine leads to more restrictive entrapment of dextran or reduction in mesh size which decreases the diffusion coefficient of dextran-FITC. These results combined with the earlier examples clearly demonstrate that the release is slower in the mixed positive and negatively-charged matrices relative to a single polymer matrix. Furthermore, the results confirm that a single phase matrix of two oppositely charged polymers has superior drug delivery capability over a matrix having a single polymer.

While this present invention has been described in detail above based on the specific embodiments thereof, it will be apparent to one skilled in the art that various changes and modifications can be made without departing from the spirit and the scope of the present invention.

What is claimed is:

1. A drug delivery device comprising a single phase matrix solution of a negatively-charged water-soluble polymer and a positively-charged water-soluble polymer, wherein said matrix solution has dispersed therein a pharmaceutically active ingredient which is different from said negatively-charged water-soluble polymer and said positively-charged water-soluble polymer.

2. The drug delivery device of claim 1, wherein said negatively-charged polymer is selected from the group consisting of succinylated collagen, carboxymethylated chitosan, hyaluronic acid, polyacrylic acid, sodium alginate, chondroitin sulfate, heparin and albumin.

3. The drug delivery device of claim 2, wherein said negatively-charged polymer is succinylated collagen or carboxymethylated chitosan.

4. The drug delivery device of claim 3, wherein said succinylated collagen or carboxymethylated chitosan is cross-linked.

5. The drug delivery device of claim 1, wherein said positively-charged polymer is selected from the group consisting of chitosan, methylated collagen, a polyamino acid, and lysozyme.

6. The drug delivery device of claim 5, wherein said polyamino acid is polylysine or polyarginine.

7. The drug delivery device of claim 5, wherein said positively-charged polymer is lysozyme.

8. The drug delivery device of claim 1, wherein said pharmaceutically active ingredient has a molecular weight of about 5,000 daltons to about 300,000 daltons.

9. The drug delivery device of claim 8, wherein said pharmaceutically active ingredient has a molecular weight of about 10,000 daltons to about 100,000 daltons.

10. The drug delivery device of claim 8, wherein said pharmaceutically active ingredient is selected from the group consisting of interferon, growth factor, antibody, interleukin, insulin, and erythropoietin.

11. The drug delivery device of claim 10, wherein said growth factor is selected from the group consisting of human growth hormone, colony stimulating factor, and bone morphogenic protein.

12. The drug delivery device of claim 8, wherein said pharmaceutically active ingredient is selected from the group consisting of Factor VIII, Factor IX, Protein C.

13. The drug delivery device of claim 1, wherein one of the polymers is cross-linked.

14. A method for sustaining release of a pharmaceutically active ingredient in a subject, comprising:
administering to a subject a drug delivery device comprising a single phase matrix solution of a negatively-charged water-soluble polymer and a positively-charged water-soluble polymer, wherein said matrix solution has dispersed therein a pharmaceutically active ingredient which is different from said negatively-charged water-soluble polymer and said positively-charged water-soluble polymer.

15. The method of claim 14, wherein said negatively-charged polymer is selected from the group consisting of succinylated collagen, carboxymethylated chitosan, hyaluronic acid, polyacrylic acid, sodium, alginate, chondroitin sulfate, heparin and albumin.

16. The method of claim 15, wherein said negatively-charged polymer is succinylated collagen or carboxymethylated chitosan.

17. The method of claim 16, wherein said negatively-charged polymer is non-cross-linked, succinylated collagen or carboxymethylated chitosan, and administrating is carried out by injecting said device into said subject.

18. The method of claim 16, wherein said negatively-charged polymer is cross-linked, succinylated collagen or carboxymethylated chitosan, and administrating is carried out by implanting said device into said subject.

19. The method of claim 14, wherein said positively-charged polymer is selected from the group consisting of chitosan, methylated collagen, a polyamino acid, and lysozyme.

20. The method of claim 19, wherein said polyamino acid is polylysine or polyarginine.

21. The method of claim 19, wherein said positively-charged polymer is lysozyme.

22. The method of claim 14, wherein said pharmaceutically active ingredient has a molecular weight of about 5,000 daltons to about 300,000 daltons.

23. The method of claim 22, wherein said pharmaceutically active ingredient has a molecular weight of about 10,000 daltons to about 100,000 daltons.

24. The method of claim 14, wherein said pharmaceutically active ingredient is selected from the group consisting of interferon, growth factor, antibody, interleukin, insulin, and erythropoietin.

25. The method of claim 24, wherein said growth factor is selected from the group consisting of Factor VIII, Factor IX, Protein C, human growth hormone, colony stimulating factor, and bone morphogenic protein.

26. The method of claim 22, wherein said pharmaceutically active ingredient is selected from the group consisting of Factor VIII, Factor IX, Protein C.

27. The method of claim 14, wherein one of the polymers is cross-linked.

28. The drug delivery device of claim 1, wherein said negatively-charged polymer is succinylated collagen and said positively-charged polymer is polylysine.

29. The method of claim 14, wherein said negatively-charged polymer is succinylated collagen and said positively-charged polymer is polylysine.

* * * * *